(12) United States Patent
Morsy et al.

(10) Patent No.: US 6,612,987 B2
(45) Date of Patent: Sep. 2, 2003

(54) APPARATUS AND METHOD FOR SELECTIVELY OPTIMIZING AN ACOUSTIC TRANSDUCER

(75) Inventors: Ahmed Morsy, Bellevue, WA (US); Andrew Robinson, Bellevue, WA (US)

(73) Assignee: Koninklijke Philips Electronics N.V. (NL)

( * ) Notice: Subject to any disclaimer, the term of this patent is extended or adjusted under 35 U.S.C. 154(b) by 0 days.

(21) Appl. No.: 10/011,160

(22) Filed: Dec. 5, 2001

(65) Prior Publication Data

US 2003/0105399 A1 Jun. 5, 2003

(51) Int. Cl.[7] ................................................. A61B 8/00
(52) U.S. Cl. ..................................................... 600/437
(58) Field of Search ................................ 310/314–317, 310/334–336; 600/437, 443, 447, 453–456, 459; 73/618–644

(56) References Cited

U.S. PATENT DOCUMENTS

| | | | | |
|---|---|---|---|---|
| 3,934,577 A | * | 1/1976 | Romani | .................. 600/453 |
| 5,198,713 A | * | 3/1993 | Suzuta | .................. 310/316 |
| 5,313,947 A | * | 5/1994 | Micco | .................. 600/455 |
| 5,603,324 A | * | 2/1997 | Oppelt et al. | .................. 600/437 |
| 6,104,670 A | | 8/2000 | Hossack et al. | .................. 367/7 |

* cited by examiner

*Primary Examiner*—Francis J. Jaworski
(74) *Attorney, Agent, or Firm*—Dorsey & Whitney LLP

(57) ABSTRACT

The invention is directed towards an apparatus and method for selectively optimizing piezoelectric elements in an ultrasound transducer assembly for a given imaging mode. In one embodiment, a variable impedance network is interposed between an ultrasound processor and a transducer assembly and may be coupled to the transducer assembly to form either a series or a parallel connection with the transducer assembly. The network may be controlled by the processor to selectively alter the characteristics of the network. In another embodiment, the variable impedance network includes a pair of serially coupled inductors and a switch that permits one of the inductors to be controllably bypassed. In still another embodiment, the network includes a tapped inductor and a switch to permit the inductor tap to be controllably selected. In still another aspect, the inductor includes a tapped inductor having multiple taps, each tap selectable by a switch to optimize the network.

20 Claims, 5 Drawing Sheets

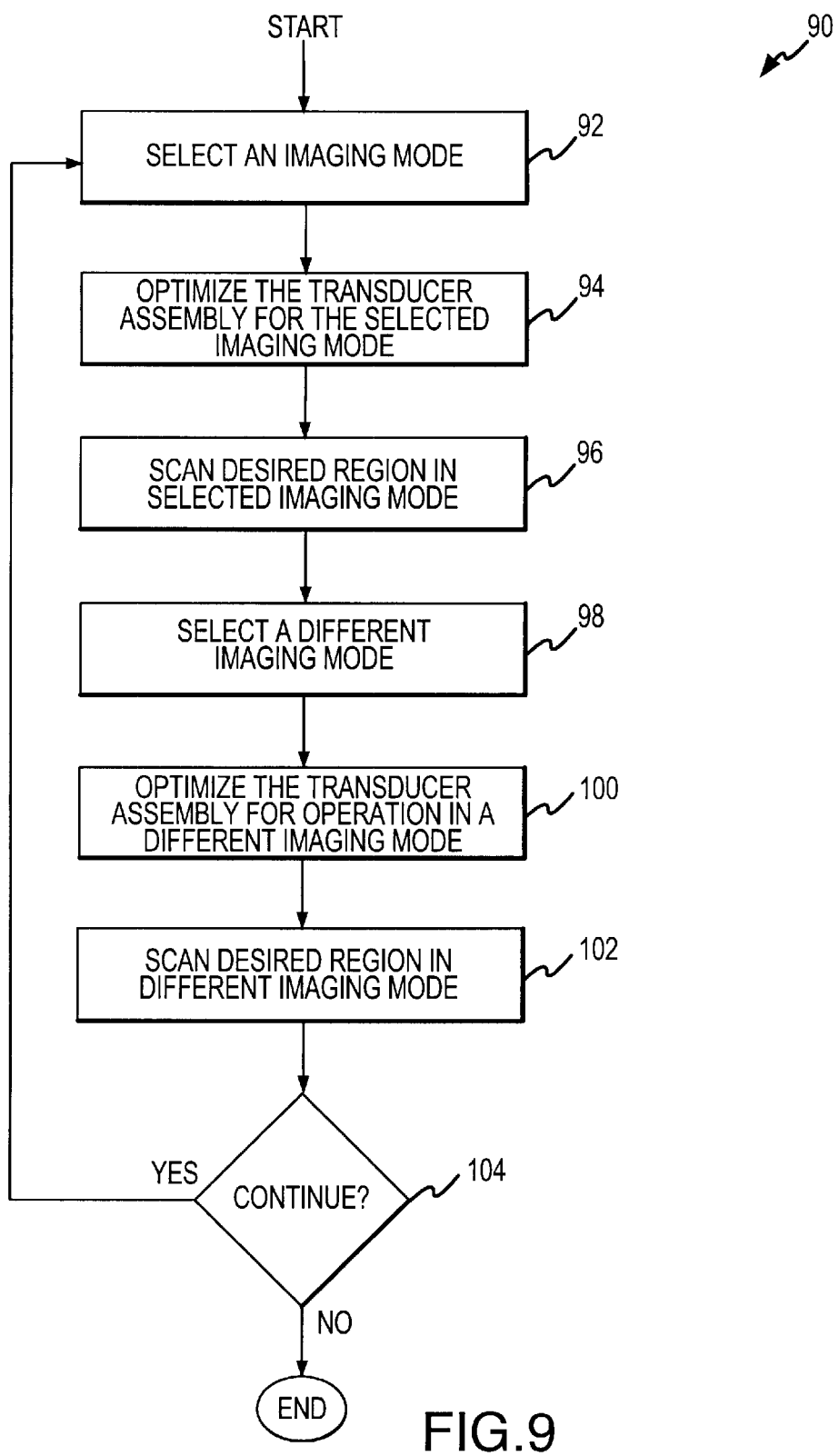

APPARATUS AND METHOD FOR SELECTIVELY OPTIMIZING AN ACOUSTIC TRANSDUCER

TECHNICAL FIELD

This invention relates generally to ultrasound imaging systems that use ultrasonic transducers to provide diagnostic information concerning the interior of the body, and more particularly, to an apparatus and method for selectively optimizing an acoustic transducer.

BACKGROUND OF THE INVENTION

Ultrasonic diagnostic imaging systems are in widespread use for performing ultrasonic imaging and measurements. For example, cardiologists, radiologists, and obstetricians use ultrasonic imaging systems to examine the heart, various abdominal organs, or a developing fetus, respectively. Diagnostic images are obtained from these systems by placing a scanhead against the skin of a patient, and actuating an ultrasonic transducer located within the scanhead to transmit ultrasonic energy through the skin and into the body of the patient. In response, ultrasonic echoes are reflected from the interior structure of the body, and the returning acoustic echoes are converted into electrical signals by the transducer in the scanhead.

FIG. 1 is a functional block diagram of an ultrasound imaging system 10 according to the prior art. The system 10 includes an ultrasound processor 11 that is coupled to a scanhead assembly 12 by a connecting cable 26. The ultrasonic processor 11 further includes a transmitter 22 that generates signals at ultrasonic frequencies for emission by the scanhead assembly 12, and a receiver 16 to process signals received by the scanhead assembly 12. In order to isolate the transmitter 22 from the scanhead assembly 12 while the receiver 16 is in operation, a transmitter isolation unit 18 decouples the transmitter 22 from the cable 26. Correspondingly, when the transmitter 22 is in operation, a receiver protection unit 19 decouples the receiver 16 from the cable 26. A controller 14 interacts with the transmitter 22, the receiver 16, the transmitter isolation unit 18 and the receiver protection unit 19 to coordinate the operation of these components. The controller 14 similarly interacts with a display system 15 to coordinate the reception of signals received by the processor 11 so that a visual image may be generated.

The scanhead assembly 12 includes a transducer assembly 28 that is comprised of one or more piezoelectric elements 30 that are capable of emitting ultrasonic pulses when excited by signals generated by the transmitter 22, and converting the reflected portions of the pulses into electrical signals that may be processed by the receiver 16. The transducer assembly 28 is coupled to the processor 11 through a tuning network 20 that tunes the assembly 28 to optimize the characteristics of the scanhead and the processor 11. The tuning network 20 may be attached to assembly 28 to form the integral scanhead assembly 12, or alternatively, the network 20 may be interposed between the assembly 28 and the processor 11 at a position along the connecting cable 26, as also shown in FIG. 1. Still further, the tuning network 20 may be positioned within the processor 11 (not shown) or within a connecting element in the connecting cable 26 (also not shown).

FIG. 2 is a partial schematic diagram of the ultrasound imaging system 10 according to the prior art. The transducer assembly 28 is serially coupled to the processor 11 through the connecting cable 26 and a tuning inductor 36. For clarity of illustration, FIG. 2 shows only a single element 30 (as shown in FIG. 1) coupled to a single connecting cable 26 by a single inductor 36. It is understood, however, that the transducer assembly 28 generally includes more than a single element 30, each of which may be coupled to the processor 11 through a separate, dedicated tuning inductor 36 and cable 26.

In general, the inductor 36 does not have an inductance value that permits the element 30 to be operated at only a single resonant condition. Instead, the inductor 36 is selected to allow the element 30 to be operated over a range of frequencies that define an acceptable operating bandwidth for the element 30 in a prescribed imaging mode. One trade-off of this approach is that a broad bandwidth for the element 30 generally results in a reduced sensitivity of the element 30 to the reflected pulses at a particular individual frequency. While somewhat reduced sensitivity of the element 30 may be acceptable when the imaging system 10 is operated, for instance, in a gray scale mode, it may have disadvantages in certain other ultrasound operating modes. For example, the system 10 may be operated in a Doppler ultrasound mode to provide an image of blood flow in an interior portion of a patient. In this imaging mode, the return signal is scattered from minute corpuscular components in the blood flow, which produces return signals that are generally greatly reduced in magnitude as compared to return signals typically encountered in the gray scale imaging mode. Increasing the magnitude of the emitted signal to produce stronger return signals cannot, in general, mitigate this disadvantage, since the magnitude of ultrasound signals cannot exceed prescribed levels that may produce cavitation effects in the interior portions of the patient's body, or produce damaging levels of tissue heating. Alternatively, dynamically changing the inductance of the inductor 36 is difficult since the inductor 36 is generally a fixed component that is positioned within a scanhead assembly, or in other portions of an ultrasound imaging system.

Accordingly, there exists a need in the art for an ultrasound system that permits optimization of a transducer assembly to achieve wide bandwidth operation for certain ultrasound operating modes and narrower bandwidth operation to be selected for other modes of operation that require higher transducer sensitivity, as well other characteristics for different modes.

SUMMARY OF THE INVENTION

The invention is directed towards an apparatus and method for selectively optimizing an ultrasound transducer assembly to provide enhanced performance in specific ultrasound modes of operation. In one aspect, a variable impedance network is positioned between an ultrasound processor and a transducer assembly and may be coupled to the transducer assembly to form either a series or a parallel connection with the transducer assembly. The variable impedance network may be controlled by the processor to selectively alter the characteristics of the network to optimize the transducer assembly for a selected operating mode. In another aspect, the variable impedance network includes a pair of serially coupled inductors and a switch that permits one of the inductors to be controllably bypassed. In still another aspect, the variable impedance network includes a tapped inductor and a switch that permits the inductor tap to be controllably selected. In still another aspect, the inductor includes a tapped inductor having more than a single tap, each tap being selected by a switch to alter the impedance of the network.

BRIEF DESCRIPTION OF THE DRAWINGS

FIG. 9 is a flow chart illustrating the steps in a method for operating an ultrasound system having a selectively variable network coupled to a transducer assembly according to still another embodiment of the invention.

DETAILED DESCRIPTION OF THE INVENTION

This invention relates generally to ultrasound imaging systems that use ultrasonic transducers to provide diagnostic information concerning the interior of the body. More particularly, the present invention relates to an apparatus and method for selectively optimizing the transducer elements in an ultrasound transducer assembly. Many of the specific details of certain embodiments of the invention are set forth in the following description and in FIGS. 3 through 9 to provide a thorough understanding of such embodiments. One skilled in the art will understand, however, that the present invention may be practiced without several of the details described in the following description. Moreover, in the following description, it is understood that the variable impedance networks disclosed in the various embodiments as herein described may be positioned, in whole or in part, within a scanhead assembly or within an ultrasound processor, as previously described. Furthermore, it is understood that the variable impedance network may be also be positioned, in whole or in part, in a connecting cable, or within removable connectors that terminate the connecting cable.

Figure 3:
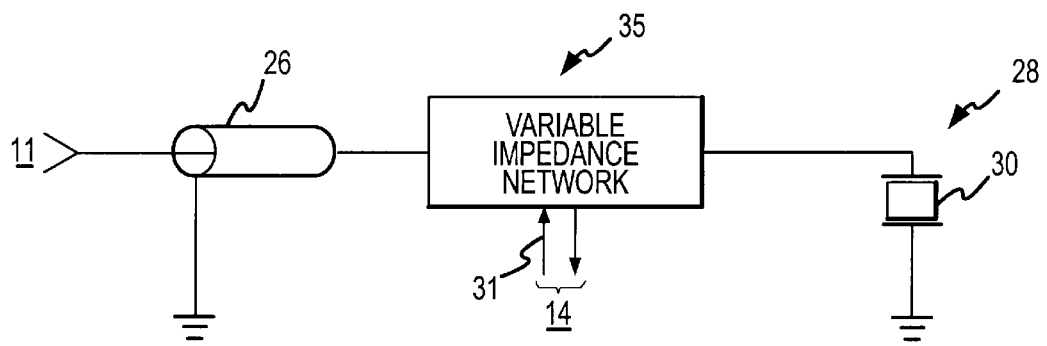
FIG. 3 is a schematic view of a network for scanhead optimization according to an embodiment of the invention.

FIG. 3 is a schematic view of a variable impedance network 35 for optimizing the piezoelectric elements in a transducer assembly according to an embodiment of the invention. The characteristics of an ultrasound system which may be optimized in a particular embodiment of the present invention include the system sensitivity, bandwidth, and pulse length, for instance The network 35 is coupled to a coaxial connecting cable 26 at one end, and a piezoelectric element 30 at an opposing end. For clarity of illustration, a single network 35 is shown that is coupled to a single connecting cable 26 and a single element 30 of a transducer assembly 28. It is understood, however, that when one or more elements 30 are present in the assembly 28, each may have a separate network 35 and be coupled to a separate connecting cable 26. The network 35 is further capable of exchanging control signals 31 with the controller 14 (as shown in FIG. 1) to controllably optimize the element 30.

Figure 1:
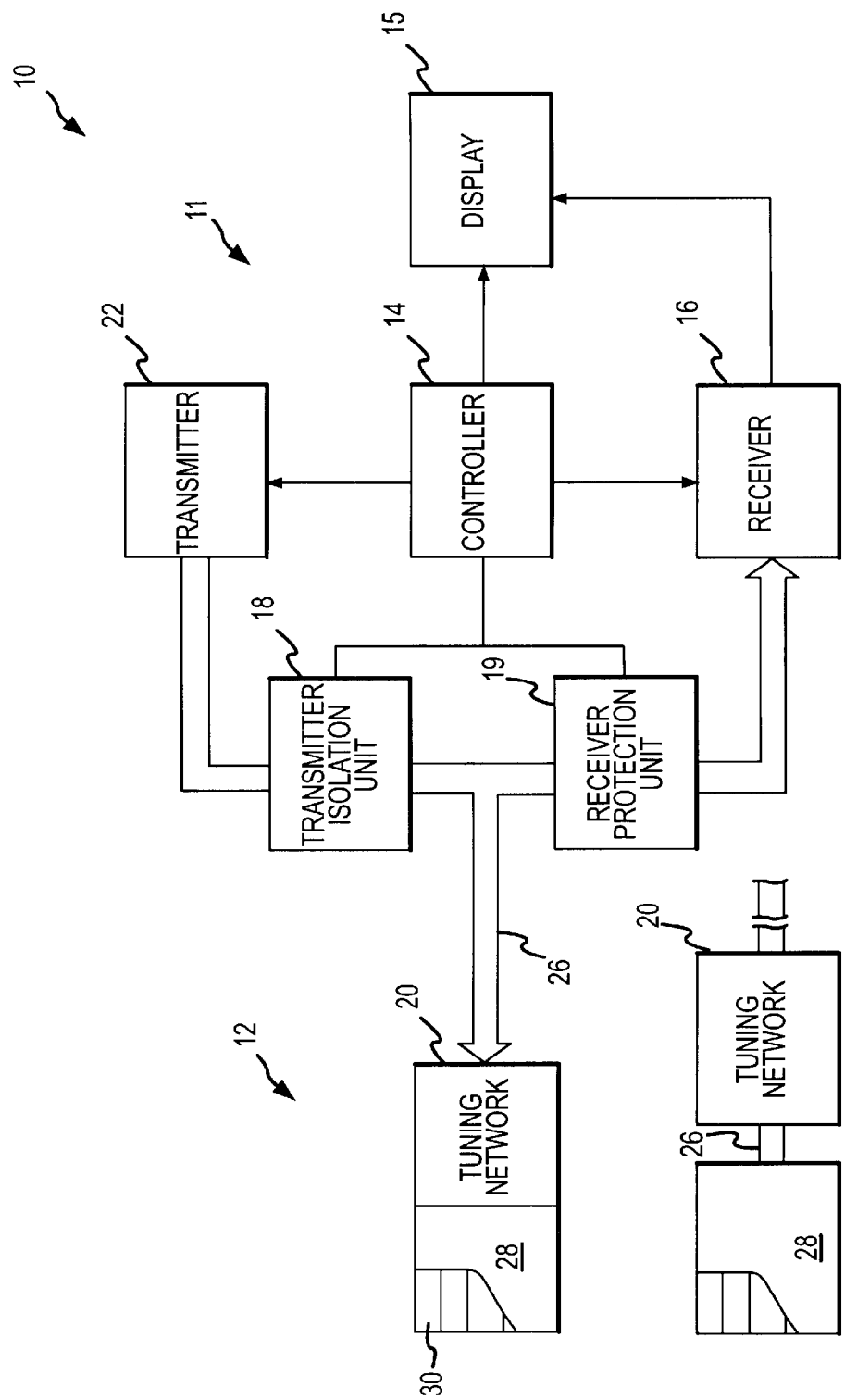
FIG. 1 is a block diagram of an ultrasonic imaging system according to the prior art.
Figure 4:
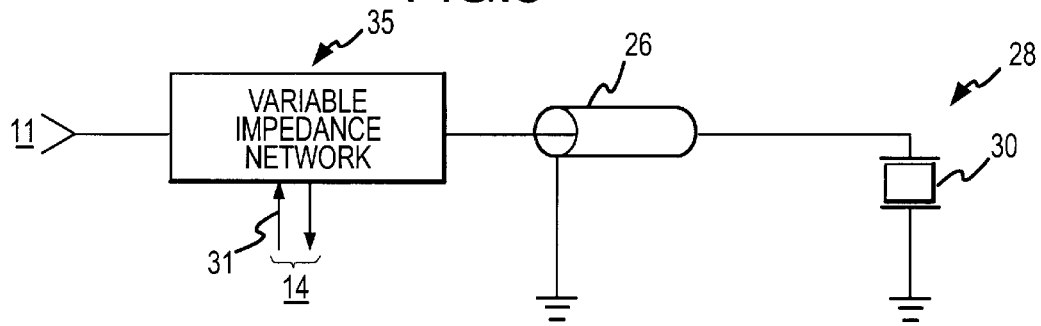
FIG. 4 is a schematic view of a network for scanhead optimization according to an embodiment of the invention.
Figure 5:
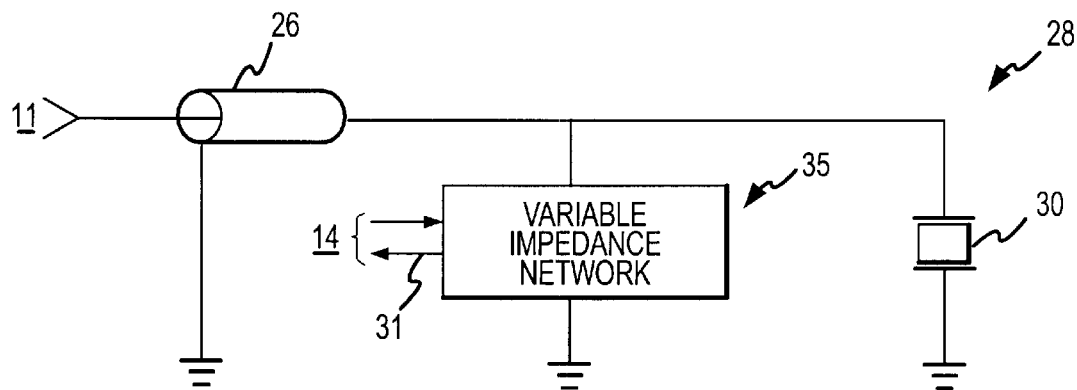
FIG. 5 is a schematic view of a network for scanhead optimization according to an embodiment of the invention.

The control signals 31 may control the network in response to an operator-initiated selection of a scan mode, or alternatively, the optimization may be selected in response to the connection of a transducer assembly 28 (also as shown in FIG. 1). In one aspect of the present embodiment, the network 35 may be coupled in series with the element 30, but positioned between the processor 11 and the connecting cable 26, as shown in FIG. 4. In a further aspect, the network 35 may be coupled in parallel with the element 30, as shown in FIG. 5. The network may also be partitioned with a variable impedance on either side of the cable 26, or distributed along the cable (not shown).

Figure 2:
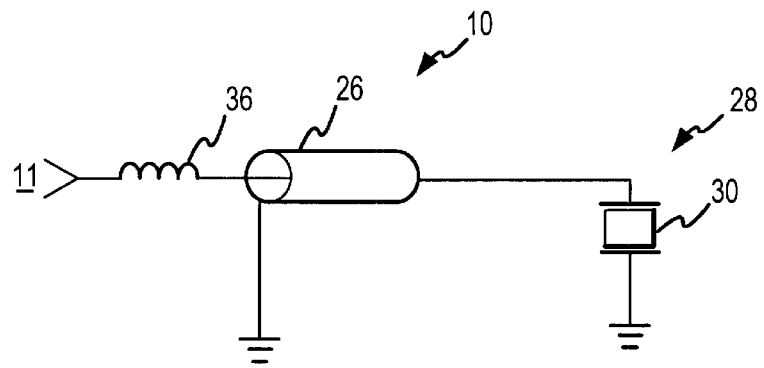
FIG. 2 is a partial schematic view of an ultrasonic imaging system according to the prior art.
Figure 6:
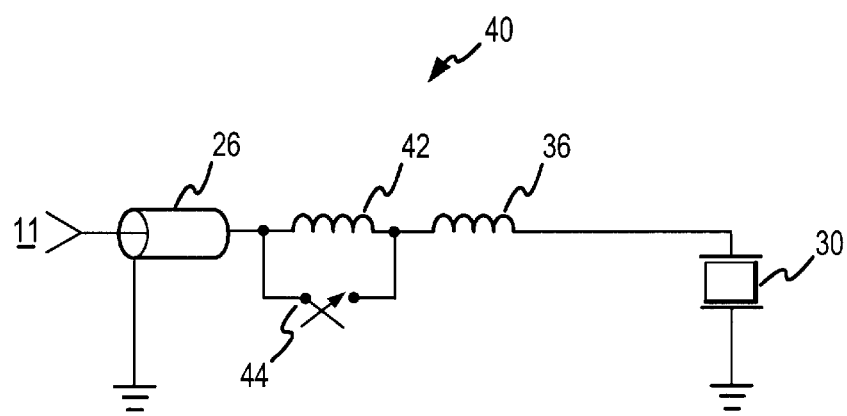
FIG. 6 is a schematic view of a network for scanhead optimization according to another embodiment of the invention.

FIG. 6 is a schematic view of a variable impedance network 40 for optimizing the piezoelectric elements in a transducer assembly according to another embodiment of the invention. The network includes an inductor 36 that is coupled in series to an auxiliary inductor 42. A single pole, single throw (SPST) switch 44 is coupled in parallel with the auxiliary inductor 42 to permit the inductor 42 to be selectively bypassed. Thus, when the switch 44 is positioned in an open state, as shown in FIG. 6, the inductance present in the network 40 consists of the sum of the inductances introduced by the matching inductor 36 and the auxiliary inductor 42. Correspondingly, when the switch 44 is positioned to the closed state, the auxiliary inductor 42 is bypassed so that the inductance introduced by the network 40 is due to the inductor 36 alone. The switch 44 may be comprised of a mechanical switch that may be remotely positioned, or alternatively, a semiconductor device, such as a MOSFET device configured as a switch may be used. Since the selection of an ultrasound imaging mode may require a change to optimize the transducer for the new mode, the switch 44 may be remotely positioned by the controller 14 (as shown in FIG. 1) when an operator interacts with the controller 14 to select an imaging mode. Alternatively, the switch 44 may be automatically positioned to the appropriate state when a connector portion (not shown in FIGS. 1 and 2) of the connecting cable 26 is coupled to the processor 11, or to the transducer assembly 28. One suitable SPST switch that may be remotely actuated is the Supertex HV202 series high voltage analog switch, available from Supertex, Inc., of Sunnyvale, Calif., although other suitable alternatives exist.

Figure 7:
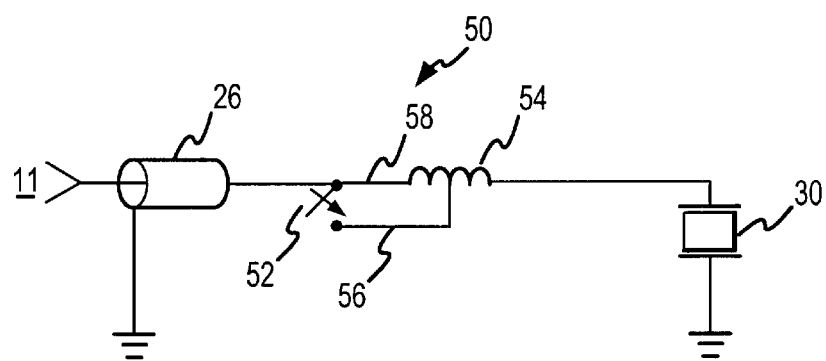
FIG. 7 is a schematic view of a network for scanhead optimization according to still another embodiment of the invention.

FIG. 7 is a schematic view of a variable impedance network 50 for optimizing the piezoelectric elements in a transducer assembly according to still another embodiment of the invention. The network 50 includes a tapped inductor 54 that is capable of selectively providing two different inductance values for the network 50. A single pole, single throw (SPST) switch 52 operates to serially couple the entire tapped inductor 54 with the element 30 through a line 58 when the switch 52 is in the open state, as shown in FIG. 7. Alternatively, a tapped portion of the inductor 54 may be serially coupled to the element 30 through a line 56 when the SPST switch 52 is positioned in a closed state. The inductance available to the variable impedance network 50 is therefore selectable by positioning the SPST switch 52 to place either the line 58 or the line 56 into the network 50.

Figure 8:
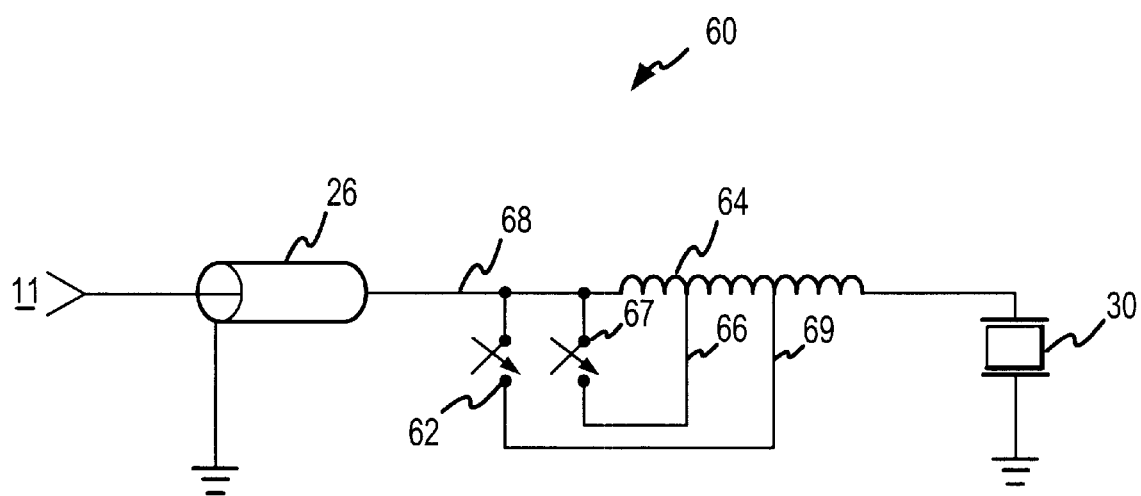
FIG. 8 is a schematic view of a network for scanhead optimization according to yet another embodiment of the invention.

FIG. 8 is a schematic view of a variable impedance network 60 for optimizing the piezoelectric elements in a transducer assembly according to yet another embodiment of the invention. The network 60 includes a tapped inductor 64 that includes a first tap 66 and a second tap 69 to permit different inductance values to be selectively inserted into the network 60 by positioning a first SPST switch 62, or a second SPST switch 67 to couple with the first tap 66, or the second tap 69. Thus, when the first SPST switch 62 is positioned in the closed state and the second SPST switch 67 is in the open state, the first SPST switch 62 couples a line 68 to the second tap 69 to introduce a first portion of the inductor 64 into the network 60. Similarly, when the second SPST switch 67 is positioned in the closed state and the first switch 62 is positioned in the open state, the second SPST switch 67 couples with the first tap 66 to introduce a second portion of the inductor 64 into the network 60. When the first SPST switch 62 and the second SPST switch 67 are both positioned in the open state, as shown in FIG. 8, the entire inductance associated with the tapped inductor 64 is inserted in the network 60. Accordingly, the inductance available to the variable impedance network 60 is selectable by positioning the SPST switches 62 or 67 to couple either the entire inductance of the inductor 64 into the network 50, or to couple a selected portion of the inductor 64 into the network 50. Although the present embodiment includes a tapped inductor 64 having a first tap 66 and a second tap 69, it is understood that an inductor having more than a pair of taps may be used, and accordingly, is within the scope of the present embodiment.

The foregoing embodiments of the invention provide variable impedance networks that may be selectively configured to electrically optimize the piezoelectric elements in an ultrasonic transducer assembly for a particular operating mode by advantageously selectively coupling additional elements into the network. Hence, the operating bandwidth or the sensitivity of the elements to reflected ultrasonic energy or the response to a particular pulse length may be altered. The selective optimizing of the piezoelectric elements in the manner described thus permits relatively wide bandwidth operation of the transducer assembly in one imaging mode, while advantageously permitting narrower bandwidth operation in other imaging modes where increased sensitivity of the transducer assembly is desired.

FIG. 9 is a flow chart illustrating the steps in a method 90 for operating an ultrasound system having a selectively variable network coupled to a transducer assembly according to still another embodiment of the invention. At step 92, an ultrasound system operator interacts with an ultrasound processor unit to select an imaging mode. Alternatively, the imaging mode may selected by other means, such as the automatic selection of an imaging mode by coupling a connector attached to the transducer assembly to the processor unit. At step 94, the variable impedance network associated with the transducer assembly selectively changes to optimize the transducer assembly based upon the image mode selected. For example, the selected imaging mode may be a gray scale imaging mode. Accordingly, the variable impedance network is configured to provide relatively wide bandwidth operation in this imaging mode. At step 96, a selected region of a patient's body is scanned in the selected imaging mode. The scanning proceeds in a wellknown manner that includes the sequential emission of ultrasonic pulses from the transducer assembly that is followed by the reception of reflected pulses by the transducer assembly. At step 98, at the option of the operator or by an automated change in system operation, a different imaging mode is selected. The different imaging mode may be, for example, a Doppler imaging mode that requires the transducer assembly to exhibit relatively higher sensitivity to a reflected portion of the ultrasonic pulses emitted by the transducer assembly. At step 100, the variable impedance network again selectively varies the transducer assembly to attain a preferred optimized condition consistent with the new selected mode. For a Doppler imaging mode, the variable impedance network will be configured to provide relatively narrower bandwidth operation to allow the transducer assembly to exhibit greater sensitivity to reflected portions of the emitted pulses. At step 102, the patient is scanned in the different imaging mode to provide ultrasound imaging information. At the completion of the ultrasound imaging, step 104 allows the ultrasound diagnostic procedure to be terminated, or alternatively, to be repeated by returning to step 92.

The foregoing embodiment advantageously allows an ultrasonic diagnostic procedure to be conducted that may include a number of imaging modes. For instance, acquisition of a colorflow image may consist of a series of transmit-receive sequences of B mode (grayscale) pulses and echoes, interleaved with transmit-receive sequences of Doppler pulses and echoes. The various imaging modes may be selected without installing or physically altering the transducer array or any other associated component, since the elements in the transducer array may be selectively affected to provide the desired sensitivity and/or bandwidth and/or pulse length characteristics required by the selected imaging mode.

What is claimed is:

1. An ultrasonic diagnostic system, comprising:
    a transducer assembly having at least one transducer element;
    a processor operatively coupled to the transducer assembly to receive signals generated by the at least one transducer element, and to transmit signals generated within the processor to the at least one element; and
    a variable impedance network electrically interposed between the processor and the at least one transducer element that includes inductive circuit elements that may be selectively and serially coupled to the at least one transducer element to electrically optimize the at least one transducer element for different imaging modes.

2. The system according to claim 1, further comprising a controller to controllably select the circuit elements in the variable impedance network.

3. The system according to claim 1, further comprising a connecting cable having a first end and an opposing second end that couples the transducer assembly to the processor.

4. The system according to claim 3 wherein the variable impedance network is positioned adjacent to the transducer assembly and coupled to the first end of the connecting cable, and the second end of the connecting cable is coupled to the processor.

5. The system according to claim 3 wherein the variable impedance network is positioned adjacent to the processor and coupled to the second end of the connecting cable, and the first end of the connecting cable is coupled to the transducer assembly.

6. The system according to claim 3 wherein the variable impedance network is interposed between the first end and the second end of the connecting cable.

7. The system according to claim 1 wherein the variable impedance network is further comprised of a first inductor having a first terminal coupled to the processor and an opposing second terminal, a second inductor having a first terminal and an opposing second terminal coupled to the at least one transducer element, the second terminal of the first inductor being coupled to the first terminal of the second inductor, and a switch coupled to the first terminal of the first inductor and the second terminal of the first inductor, the switch being positionable to selectively bypass the first inductor.

8. The system according to claim 1 wherein the variable impedance network is further comprised of a tapped inductor having a first terminal coupled to the processor and an opposing second terminal coupled to the at least one transducer element, the tapped inductor further having a tap positioned intermediately between the first and second terminals, and further wherein a switch is coupled to the first terminal and the tap, the switch being positionable to couple the processor to either the first terminal or the tap.

9. The system according to claim 1 wherein the variable impedance network is further comprised of a tapped inductor having a first terminal coupled to the processor and a second terminal coupled to the at least one transducer element, the tapped inductor further having a plurality of taps positioned at intermediate locations between the first terminal and the second terminal, and further wherein a plurality of switches each having a first end and a second end are coupled to the first terminal at the respective first ends and each second end being coupled to a single tap, each switch being positionable to couple the processor to a selected one of the plurality of taps.

10. A method for selectively optimizing a transducer element in an ultrasound system capable of operation in more than a single imaging mode, comprising:

selecting an imaging mode;

identifying a preferred operating characteristic for the selected mode; and serially coupling a selected inductance element to the transducer element to attain the preferred operating characteristic.

11. The method according to claim 10 wherein selecting an imaging mode is further comprised of selecting an imaging mode by manually entering an imaging mode on an input device coupled to the ultrasound system.

12. The method according to claim 10 wherein coupling a selected impedance element is further comprised of selectively coupling an inductor to the transducer element.

13. The method according to claim 12 wherein selectively coupling an inductor to the transducer element is further comprised of selecting a tap on a tapped inductor.

14. The method according to claim 12 wherein selectively coupling an inductor to the transducer element is further comprised of coupling a first inductor to the transducer element while bypassing a second inductor.

15. The method according to claim 10 wherein coupling a selected impedance element to the transducer element is further comprised of positioning a switch to select the impedance element.

16. A method for operating an ultrasound system having a variable network coupled to a transducer assembly, comprising:

selecting a first imaging mode;

configuring the variable network to serially couple a first inductance element to the network to attain a first imaging characteristic;

scanning a region in the first imaging mode;

selecting a second imaging mode different from the first imaging mode;

configuring the variable network to serially couple a second inductance element to the network to attain a second imaging characteristic; and scanning a region in the second imaging mode.

17. The method according to claim 16 wherein selecting a first imaging mode is further comprised of selecting a gray scale imaging mode, and wherein selecting a second imaging mode is further comprised of selecting a Doppler imaging mode.

18. The method according to claim 16 wherein configuring the variable network to attain a first imaging characteristic further comprises selecting a first operating bandwidth, and wherein configuring the variable network to attain a second imaging characteristic further comprises selecting a secondoperating bandwidth.

19. The method according to claim 16 wherein configuring the variable network to attain a first imaging characteristic further comprises obtaining a first sensitivity, and wherein configuring the variable network to attain a second imaging characteristic further comprises obtaining a second sensitivity.

20. The method according to claim 16 wherein configuring the variable network to attain a first imaging characteristic further comprises obtaining a first pulse length response, and wherein configuring the variable network to attain a second imaging characteristic further comprises obtaining a second pulse length response.

* * * * *